(12) United States Patent
Valtonen

(10) Patent No.: US 8,456,298 B2
(45) Date of Patent: Jun. 4, 2013

(54) APPARATUS AND METHOD FOR PORTABLE TRACKING

(76) Inventor: Timo Valtonen, Siuntio (FI)

( * ) Notice: Subject to any disclaimer, the term of this patent is extended or adjusted under 35 U.S.C. 154(b) by 401 days.

(21) Appl. No.: 12/917,704

(22) Filed: Nov. 2, 2010

(65) Prior Publication Data

US 2012/0105225 A1     May 3, 2012

(51) Int. Cl.
*G08B 1/08*     (2006.01)
(52) U.S. Cl.
USPC ............. 340/539.13; 340/539.31; 340/5.3; 340/8.1; 340/10.41; 340/568.1; 340/686.6; 340/693.5; 340/573.1
(58) Field of Classification Search
USPC ............ 340/539.13, 539.31, 5.3, 8.1, 10.41, 340/568.1, 573.1, 686.6, 693.5
See application file for complete search history.

(56) References Cited

U.S. PATENT DOCUMENTS

| | | | |
|---|---|---|---|
| 6,362,778 B2 * | 3/2002 | Neher | 342/357.75 |
| 6,529,131 B2 * | 3/2003 | Wentworth | 340/573.1 |
| 6,972,684 B2 | 12/2005 | Copley | |
| 7,534,206 B1 | 5/2009 | Lovitt et al. | |
| 7,619,533 B2 | 11/2009 | Crucilla | |
| 2004/0046667 A1 | 3/2004 | Copley | |
| 2009/0017911 A1 | 1/2009 | Miyazaki | |
| 2009/0289844 A1 * | 11/2009 | Palsgrove et al. | 342/357.07 |
| 2009/0325703 A1 | 12/2009 | Suzuki et al. | |

* cited by examiner

*Primary Examiner* — Tai T Nguyen
(74) *Attorney, Agent, or Firm* — Ziegler IP Law Group, LLC

(57) ABSTRACT

A method for tracking movements in a portable tracking apparatus includes a movement sensor. Virtual object position information is generated and local movement instructions for a user of the portable tracking apparatus is determined based on the generated virtual object position information. The local movement instructions are presented only non-visually to the user and movement of the portable tracking apparatus is determined using the movement sensor. A non-visual feedback is presented to the user of the portable tracking apparatus based on the determined movement of the portable tracking apparatus.

17 Claims, 6 Drawing Sheets

APPARATUS AND METHOD FOR PORTABLE TRACKING

BACKGROUND

1. Field

The aspects of the disclosed embodiments generally relate to portable tracking apparatus and method for tracking and particularly, though not exclusively, to portable safety and exercise apparatus which tracks and monitors movement and exercise of a user of the portable safety and exercise apparatus and providing moving instructions to the user.

2. Brief Description of Related Developments

Portable personal training devices have been developed to assist users in monitoring and recording certain performance values while they train and exercise. Such device can be worn on a user's wrist or fist, includes a GPS receiver, and is operable to continuously monitor and track the user's heart rate, speed, distance traveled or pace.

In game systems, game controllers provided with vibrators, such as motors, have been used. A user can be given a sense of reality by having the vibrator driven as game progresses.

The use of a movement of a game controller as game operation data input to an external game device is realized by installing a motion sensor in the game controller. The external game device comprises a processor and memory to store and perform the game software and furthermore a display for presenting the game status and visual information to the user. Loudspeaker or other audio means are included for audio information providing to the user. When the user moves the game controller, the motion sensor detects, for example, the inclination and the rotation of the game controller, and by transmitting the detected value to an external game device, game operation data different from the conventional user's button manipulation data can be generated. For example, in a racing game, by treating a game controller as if it were a steering wheel of the car, a user can play a game with more realistic feeling compared to the feeling while operating with buttons.

SUMMARY

According to a first example aspect of the disclosed embodiments there is provided a method for tracking movements in a portable tracking apparatus including a movement sensor, the method comprising:

generating virtual object position information;

determining local movement instructions for a user of the portable tracking apparatus based on the generated virtual object position information;

presenting only non-visually the local movement instructions to the user;

determining movement of the portable tracking apparatus using the movement sensor; and presenting a non-visual feedback to the user of the portable tracking apparatus based on the determined movement of the portable tracking apparatus.

In certain example embodiments of the disclosure, the position of the portable tracking apparatus may be determined using at least one of the following: global positioning system, cellular positioning system, non-cellular positioning system and motion sensor. The virtual object position information may be a virtual object of a game application, a virtual route for the user to follow or a virtual waypoint of the virtual route. The virtual object position information may be generated by a remote apparatus connected remotely to the portable tracking apparatus.

The determined movement of the portable tracking apparatus may comprise at least one of the following: determining an angle of the movement; determining a speed of the movement; determining a length of the movement; determining time lapsed for the movement; determining timing of the movement; determining trajectory of the movement; and determining a position after the movement.

The non-visual feedback to the user may further be based on at least one of the following: deviation of the user from the virtual route or from the virtual waypoint; time lapsed; direction of the user on the virtual route; a relation of the determined movement to the virtual object position information of a game application. The relation of the determined movement to the virtual object position information of a game application may be based on at least one of the following: timing of the determined movement; and direction of the movement.

The method may further comprise presenting the local movement instructions and feedback using audio tones or tactile feedback. The movement sensor may be an accelometer or a gyro.

The method may further comprise determining a starting position of the user in a game application based on the determined position of the portable tracking apparatus; determining a virtual game object position based on the generated virtual object position information; and generating audio tones for the user based on the determined local non-visual movement instructions and feedback.

The method may further comprise determining a starting position of the user for a virtual route comprising at least one waypoint in a security application based on the determined position of the portable tracking apparatus; determining virtual route waypoint position based on the generated virtual object position information; generating audio tones for the user based on the determined local non-visual movement instructions and feedback; determining a deviation of the user position compared to the virtual route and updating the determined local non-visual feedback if the deviation exceeds a threshold set by the security application; and determining a target time for the user to reach the determined waypoint and calculating time spent for the user; and updating the determined local non-visual feedback if the time spent exceeds the target time.

According to a second aspect of the disclosed embodiments there is provided a portable tracking apparatus comprising:

a loudspeaker configured to present non-visual movement instructions and feedback to a user of the portable tracking apparatus;

a movement sensor operative to detect a movement of the portable tracking apparatus;

at least one processor;

at least one memory including computer program code, the at least one memory and the computer program code configured to, with the at least one processor, cause the apparatus at least to perform:

generate virtual object position information;

determine local movement instructions for the user based on the generated virtual object position information;

present only non-visually the local movement instructions to the user;

determine movement of the portable tracking apparatus using the movement sensor; and present a non-visual feedback to the user of the portable tracking apparatus based on the determined movement of the portable tracking apparatus.

The apparatus may further comprise a tamper detector configured to detect an attempt to remove the portable tracking apparatus from the user body. The tamper detector may comprise at least one of the following: a thermal sensor for sensing body temperature of the user and a wire through a strap of the portable tracking apparatus.

According to a third aspect of the disclosed embodiments there is provided a computer program embodied on a computer readable medium comprising computer executable program code which, when executed by at least one processor of an apparatus, causes the apparatus to perform:

generate virtual object position information;

determine local movement instructions for the user based on the generated virtual object position information;

present only non-visually the local movement instructions to the user;

determine movement of the portable tracking apparatus using the movement sensor; and present a non-visual feedback to the user of the portable tracking apparatus based on the determined movement of the portable tracking apparatus.

Any foregoing memory medium may comprise digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

Different non-binding example aspects of the disclosed embodiments have been illustrated in the foregoing. The above embodiments are used merely to explain selected aspects or steps that may be utilized in implementations of the present invention. Some embodiments may be presented only with reference to certain example aspects. It should be appreciated that corresponding embodiments may apply to other example aspects as well.

BRIEF DESCRIPTION OF THE DRAWINGS

The aspects of the disclosed embodiments will be described, by way of example only, with reference to the accompanying drawings, in which.

DETAILED DESCRIPTION OF THE DISCLOSED EMBODIMENTS

In the following description, like numbers denote like elements.

Figure 1:
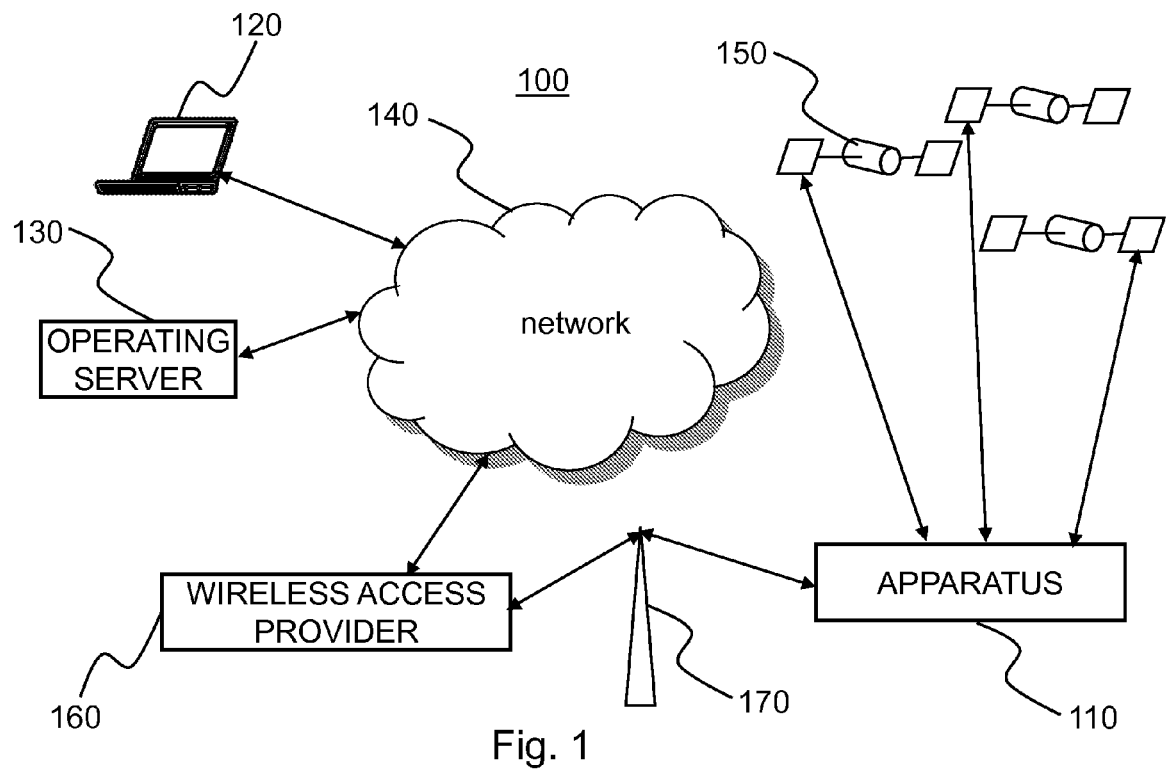
FIG. 1 shows some details of the system architecture incorporating aspects of the disclosed embodiments.

FIG. 1 shows some details of the system architecture in accordance with an example embodiment of the disclosure.

System 100 includes a portable tracking apparatus 110 for tracking a monitored individual, a wireless access provider system 160, a computer network 140 operatively coupled to the wireless access provider system 160, and monitoring apparatus 120 operatively coupled to the computer network 140. Wireless access provider 160 may contain a network of radio nodes 170 providing a wireless access for the portable tracking apparatus 110. As depicted in FIG. 1, an operating server 130 is operatively coupled to the computer network 140.

In system 100, the portable tracking apparatus 110 communicates with the operating system 130 and determines its location through radio nodes 170 that could be cell phone towers or wireless local area network access points, for example, and operatively coupled to the wireless access provider system 160. As shown in FIG. 1, portable tracking apparatus 110 communicates with the operating server 130 through the radio nodes 170. The monitoring apparatus 120 can include, but are not limited to, both analog and digital cell phones, personal digital assistants (PDAs), laptop computers, desktop computers and the like. In one embodiment, the portable tracking apparatus 110 are cell phones. Moreover, the portable tracking apparatus 110 may contain a separate positioning device or such functionality may be integrated to the portable tracking apparatus 110.

The operating server 130 is used to track and store the location of monitored individual and contain the relevant user related data for the individual. The monitored individuals can include, but are not limited to, children, senior citizen, Alzheimer patients, persons with overweight and other persons to whom someone wishes to track or improve exercise. The relevant user related data may be stored in the operating server 130.

In one embodiment, the communication between the portable tracking apparatus 110 and the computer network 140 is carried out by the wireless access provider system 160. The portable tracking apparatus 110 comprises a communication interface for this purpose. The communication interface module 250 implements at least part of the user data radio discussed in connection with various aspects of the disclosed embodiments. The communication interface module may be, e.g., a radio interface module, such as a WLAN, Bluetooth, GSM/GPRS, CDMA, WCDMA, or LTE (Long Term Evolution) radio module. The communication interface module may be integrated into the apparatus or into an adapter, card or the like that may be inserted into a suitable slot or port of the apparatus. The communication interface module may support one radio interface technology or a plurality of technologies.

The wireless access provider system 160 is operable to locate the portable tracking apparatus 110 and transmit the location to the operating server 130. The location of portable tracking apparatus 110 can be determined through angle of arrival to radio nodes 170, time of arrival to towers 170, through assisted global positioning system (GPS) via satellites 150, a combination of these, and in other manners as generally know to those skilled in the art. In one embodiment, the portable tracking apparatus 110 may determine its own location independently and transmit the location to the operating server 130 via the wireless access provider 160 through the radio nodes 170.

A plurality of satellites 150 are in orbit about the Earth. The orbit of each satellite 150 is not necessarily synchronous with the orbits of other satellites and, in fact, is likely asynchronous. A global positioning system receiver apparatus 110 such as the ones described in connection with aspects of the disclosed embodiments is shown receiving spread spectrum global positioning system satellite signals from the various satellites 150.

Figure 2:
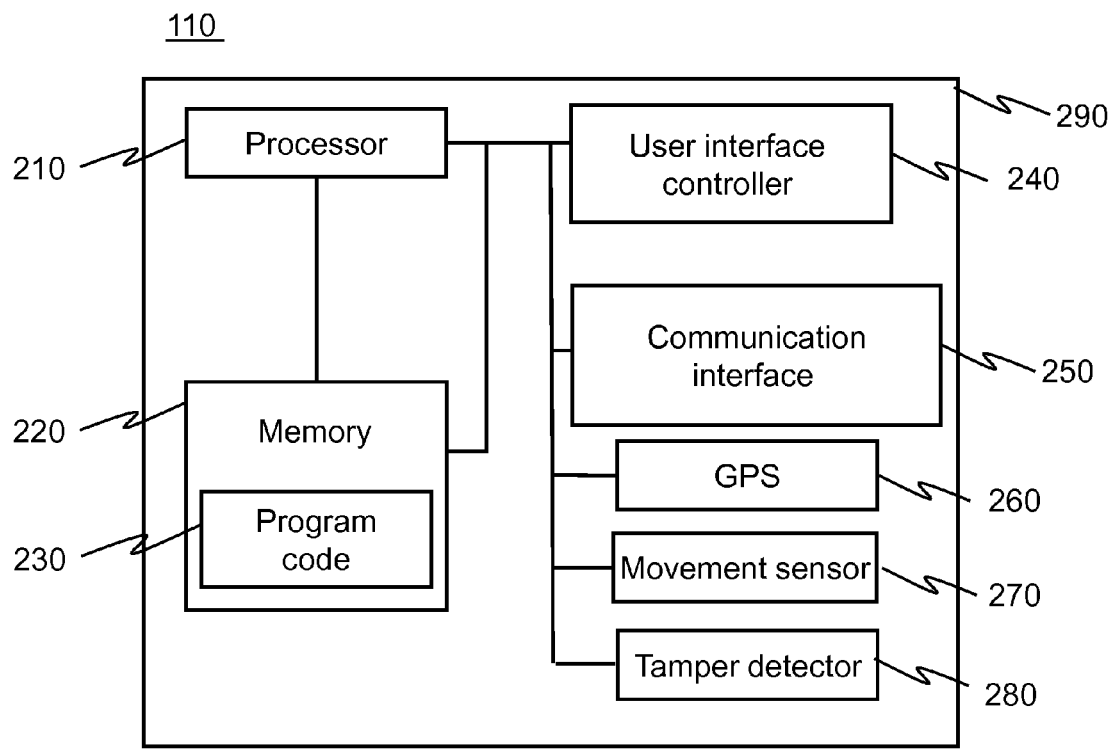
FIG. 2 presents an example block diagram of a portable tracking apparatus incorporating aspects of the disclosed embodiments.

FIG. 2 presents an example block diagram of a portable tracking apparatus 110 in which various aspects of the disclosed embodiments may be applied.

The portable tracking apparatus 110 may contain a communication interface module 250, a processor 210 coupled to the communication interface module 250, and a memory 220 coupled to the processor 210. The apparatus further comprises software 230 stored in the memory 220 and operable to be loaded into and executed in the processor 210. The software 230 may comprise one or more software modules and can be in the form of a computer program product. The apparatus 110 further comprises a user interface controller 240 coupled to the processor 210.

The communication interface module 250 implements at least part of the user data radio discussed in connection with various embodiments of the disclosure. The communication interface module 250 may be, e.g., a radio interface module, such as a WLAN, Bluetooth, GSM/GPRS, CDMA, WCDMA, or LTE (Long Term Evolution) radio module. The communication interface module 250 may be integrated into the apparatus 110 or into an adapter, card or the like that may be inserted into a suitable slot or port of the apparatus 110. The communication interface module 850 may support one radio interface technology or a plurality of technologies. FIG. 2 shows one communication interface module 250, but the apparatus 110 may comprise a plurality of communication interface modules 250.

The processor 210 may be, e.g., a central processing unit (CPU), a microprocessor, a digital signal processor (DSP), a graphics processing unit, or the like. FIG. 2 shows one processor 210, but the apparatus 800 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The apparatus 110 may comprise a plurality of memories. The memory 220 may be constructed as a part of the apparatus 110 or a user may insert it into a slot, port, or the like of the apparatus 110. The memory 220 may serve the sole purpose of storing data, or it may be constructed as a part of an apparatus serving other purposes, such as processing data.

The user interface controller 240 may comprise circuitry for receiving input from a user of the apparatus 110, e.g., via a keyboard, graphical user interface shown on the display of the apparatus 110, speech recognition circuitry, or an accessory device, such as a headset, and for providing output to the user via, e.g., a graphical user interface, vibrator or a loudspeaker.

The location determining component 260 is preferably a global positioning system (GPS) receiver, and provides, in a substantially conventional manner, geographic location information for the portable tracking apparatus 110. In general, the global positioning system is a satellite-based radio navigation system capable of determining continuous position, velocity, time, and direction information for an unlimited number of users.

The global positioning system is implemented when an apparatus specially equipped to receive global positioning system data begins scanning radio frequencies for global positioning system satellite signals. Upon receiving a radio signal from a global positioning system satellite, the apparatus can determine the precise location of that satellite via one of different conventional methods. The apparatus will continue scanning for signals until it has acquired at least three different satellite signals. Implementing geometrical triangulation, the receiver utilizes the three known positions to determine its own two-dimensional position relative to the satellites. Acquiring a fourth satellite signal will allow the receiving apparatus to calculate its three-dimensional position by the same geometrical calculation. An unlimited number of users can update the positioning and velocity data in real time on a continuous basis.

Although global positioning system enabled apparatuses are often used to describe navigational devices, it will be appreciated that satellites need not be used to determine a geographic position of a receiving unit since any receiving apparatus capable of receiving the location from at least three transmitting locations can perform basic triangulation calculations to determine the relative position of the receiving apparatus with respect to the transmitting locations. For example, cellular towers or any customized transmitting radio frequency towers can be used instead of satellites. With such a configuration, any standard geometric triangulation algorithm can be used to determine the exact location of the receiving unit. In this way, personal hand held devices, cell phones, intelligent appliances, intelligent apparel, and others can be readily located geographically, if appropriately equipped to be a receiving unit.

The spread spectrum signals continuously transmitted from each satellite 150 utilize a highly accurate frequency standard accomplished with an extremely accurate atomic clock. Each satellite 150, as part of its data signal transmission, transmits a data stream indicative of that particular satellite. The device 110 must acquire spread spectrum global positioning system satellite signals from at least three satellites for the global positioning system receiver apparatus to calculate its two-dimensional position by triangulation. Acquisition of an additional signal, resulting in signals from a total of four satellites, permits the device 110 to calculate its three-dimensional position.

The location determining component 260 may include one or more processors, controllers, or other computing devices and memory for storing information accessed and/or generated by the processors or other computing devices. The location determining component 260 is operable to receive navigational signals from the global positioning system satellites 150 to calculate a position of the portable tracking apparatus 110 as a function of the signals. The location determining component 260 is also operable to calculate a route to a desired location, provide instructions to navigate to the desired location, and to execute other functions described herein. The memory may store cartographic data and routing used by or generated by the location determining component's computing devices. The memory may be integral with the location determining component 260, stand-alone memory, or a combination of both. The memory may include, for example, removable cards.

The location determining component 260 also includes an antenna, which is preferably positioned within the housing of the apparatus in such a position to assist the location determining component in receiving signals. The antenna is preferably a global positioning system patch antenna or helical antenna but may be any other type of antenna that can be used with navigational devices. The antenna may be mounted directly on or in the housing or may be mounted external to the housing. The antenna is preferably protected from adverse conditions, such as those described above, by being entirely enclosed within the housing. Additionally, any harmful physical contact that can occur from a user's accidental contact with a conventional, pointed, antenna is eliminated, as the antenna has no sharp points protruding from the housing. Furthermore, the placement of the antenna adjacent to the display provides the antenna with adequate reception, regardless of the user's physical alignment, as the antenna is always orientated away from the user. Alternatively, the antenna may be operable to broadcast signals and may be positioned elsewhere within the housing or external to the housing.

A skilled person appreciates that in addition to the elements shown in FIG. 2, the apparatus 110 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the apparatus 110 may comprise a disposable or rechargeable battery (not shown) for powering the apparatus 110 when external power if external power supply is not available.

The portable tracking apparatus 110 may also include a number of I/O ports that permit data and other information to be transferred locally to and from the portable tracking apparatus 110. The I/O ports may include a card slot for receiving removable cards and a USB port for coupling with a USB cable connected to another computing device such as monitoring apparatus 120.

The housing 290 is preferably constructed from a suitable lightweight and impact-resistant material such as, for example, plastic, nylon, aluminum, or any combination thereof. The housing 290 preferably includes one or more appropriate gaskets or seals to make it substantially waterproof or resistant. The housing 290 may include a location for a battery, or other power source, associated with the portable tracking apparatus 110. Though shown as being substantially elongated, the housing 290 may take any suitable shape or size, including, for example, ergonomic shapes molded to substantially correspond to a portion of the user's forearm whereupon or against which the housing 290 is meant to rest.

The elongated shape of the housing 290 allows the portable tracking apparatus 110 to be securely supported by the user's forearm, fist or wrist such that the portable tracking apparatus 110 remains securely attached to the user, even during exercise or other periods of activity. The shape and dimensions of the housing 290 also allow the user to operate the portable tracking apparatus 110 with one hand, as the housing 290 may be gripped by the user's fingers while inputs described below are operated by the user's thumb. Additionally, the housing 290 has a large surface area to contain the components shown in FIG. 2 and a generally flat, rounded, profile to reduce harmful contact of the device 110 to the user or an external element.

The orientation of the portable tracking apparatus 110 may be calculated using a movement sensor 270. Such a movement sensor 270 may be an acceleration sensor or a gyroscope 270 or such. For example, when the portable tracking apparatus is used in gaming mode, the portable tracking apparatus 110 controls a game character in accordance with movement of the portable tracking apparatus 110. Specifically, data representing an action of wielding something is generated based on an output from the acceleration sensor, and data representing an orientation of something is generated based on an output from the gyroscope.

The portable tracking apparatus 110 may be wearable by the monitored person and may periodically transmit a status signal to the operating server 130. In one embodiment, the portable tracking apparatus is an arm bracelet attached to the arm of the monitored person.

As shown, the portable tracking apparatus 110 may include a tamper evidence detector 280 for detecting the monitored person or some other person tampering with the apparatus 110 in an attempt to remove the wearable portable tracking apparatus 110. The tamper evidence detector 280 may include, but is not limited to, a thermal sensor for sensing body temperature and a wire through a strap that secures the wearable portable tracking apparatus 110 to the monitored person.

The portable tracking apparatus 110 is suited also for use by persons trying to lose weight and/or improve their general fitness level while exercising, and to provide security features for the persons using the portable tracking apparatus. Security features may include tracking and surveying the user of the portable tracking apparatus and defining routes and time schedules for following the routes.

The aspects of the disclosed embodiments can be implemented in hardware, software, firmware, or a combination thereof, but is preferably implemented with the components illustrated in FIGS. 1 and 2. Specifically, according to one embodiment, the portable tracking apparatus 110 broadly comprises a communication interface 250; a location determining component 260; a loudspeaker 250, a motion sensor 270, one or more input/output devices 220, 280, and an elongated housing 290, which encloses and protects the other components from moisture, vibration, and impact associated with the exercise or movement of the user.

Figure 3:
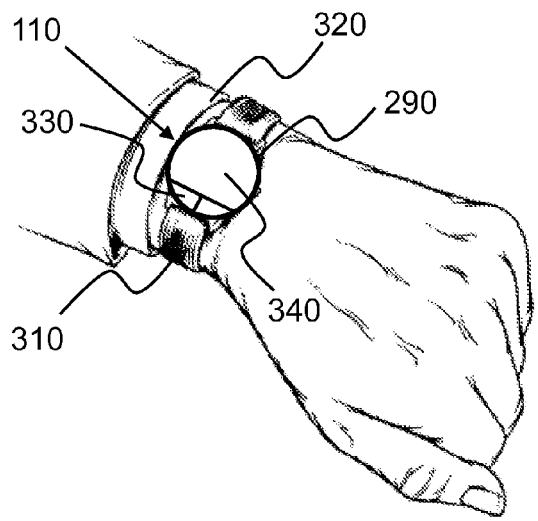
FIG. 3 presents an example of a portable tracking apparatus incorporating aspects of the disclosed embodiments, attached to a user.

FIG. 3 presents an example of a portable tracking apparatus attached to a user. The portable tracking apparatus 110 may also include a strap 310, which removably secures the housing 290 to the user's forearm, fist or wrist 320. The housing 290 may be secured also to other parts of the user with the strap 310, for example to an upper arm, a leg, an ankle or some other part of the user's foot. Navigation buttons 330 may be placed on any visible side of the housing 290 providing easy access for the user. Navigation buttons 330 may comprise for example up-button, down-button, select-button and cancel-button. Portable tracking apparatus 110 may also comprise a display 340 that may also be a touch display 340. The strap 310 is preferably made of lightweight and resilient fabric, such that the strap may encircle the user's arm without discomfort while still adequately securing the housing 290 to the user's forearm. The strap 310 is removably secured to the housing 290 by the attachment of securing elements to connecting elements. The connecting elements and securing elements may be any conventional reciprocal connecting and securing pair, such as a hooks, latches, clamps, snaps, buttons, etc. The strap 310 is attached to the user's forearm by encircling the strap around the user's forearm and securing the strap 310 to itself using hooks, latches, clamps, or other conventional fastening elements. Alternatively, the strap 310 may be configured to attach to other parts of the user, such as the user's leg, waist, fist, wrist, or upper arm. The shape and the size of the apparatus 110 are presented as wristwatch type of apparatus in FIG. 3. However, the apparatus 110 may be of any shape and size suitable for attaching to a user body part.

Figure 4:
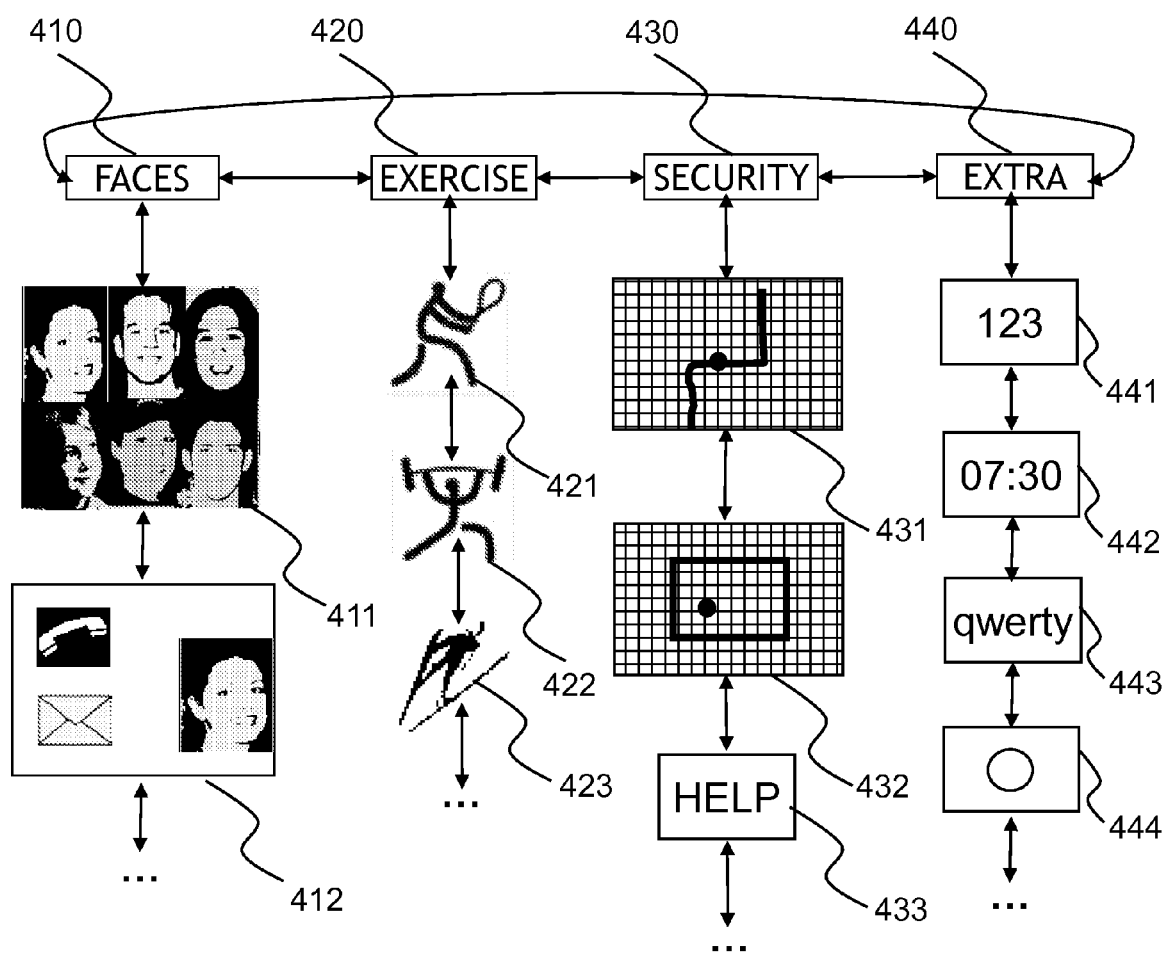
FIG. 4 shows an example of different functionalities of the portable tracking apparatus incorporating aspects of the disclosed embodiments.

FIG. 4 shows exemplary embodiment for different functionalities of the portable tracking apparatus 110. Because of a very limited display size of the apparatus 110, the user interface logic must be straight forward and simple. In one embodiment, the user interface logic comprises at least one functionality 410-440. In FIG. 4 there are four example functionalities described. User may move from one functionality 410-440 to another by using left/right navigation buttons 330 or touch display 340. In certain functionality 410-440, the movement between certain applications by pressing up/down navigation buttons 330 or touch display 340.

First functionality may be called FACES 410. FACES 410 may be a communication suite, where all communication is centered around people's faces. Such communication may be call making or call receiving, smiley/mood message/gesture sending, short message sending (using qwerty or letter input with finger). Faces used in FACES can be edited from the client application running operated by the monitoring apparatus 120.

Application 411 shows the pre-installed figures of the available persons to be called. User may select the desired person by selecting from the touch display 340 or by using the navigation buttons 330. Face-based selection makes the operation easy even for a small child that cannot read. This enhances the security for the child as well. After selecting the desired person, application 412 is showed to the user, where some further selections are made available. Such selections may be for example call activation or text message editor activation. Scrolling of FACES functionality applications 411,412 may continue up/down until the loop ends and the first application 411 is shown again.

In one embodiment of the, a second functionality 420 is an exercise functionality called EXERCISE in FIG. 4. EXERCISE 420 may be an exercise suite providing games and trainings, for example. Exercise suite applications 421-423 may feature measuring steps, distance or time spent outdoors. Furthermore, game applications may feature movement or acceleration detection for jumping, shaking, hopping or any moving detection, as well as position detection. Location detection enables route and trail tagging, respectively. Geocache gaming may also be featured. When the user selects EXERCISE 420 functionality, a scrollable list of applications 421-423 is shown. User can scroll the list up/down using navigation buttons 330 or the touch display 340 and select the desired exercise application 421-423.

In one embodiment, a third functionality 430 is a security functionality called SECURITY in FIG. 4. SECURITY 430 may be a security suite providing security and tracking applications 431-433, for example. Such applications 431-433 may be, but not limited to, safe route 431, safe area 432, help 433 and arrival information (not shown). Safe route 431 is an application, in which remote client may set and monitor a specific route for the user of the portable tracking apparatus 110 to follow. In safe area application 432, a certain safe area is defined by the client for the portable user apparatus. Help application 433 may be an emergency application that enables direct call with location info to the client or directly to the local emergency number. Arrival information enables an automatic acknowledgement of arrival to the client, when portable tracking apparatus is arriving to a certain defined place. Furthermore, a time criteria may be set providing the possibility to include time criteria for the monitoring as well. In case the portable tracking apparatus user is not traveling in certain route at certain speed as specified by the client, an alarm may be triggered. By doing this, the client is being informed in case the portable tracking apparatus user is moving too slow. This might mean that the user of the portable tracking apparatus is in danger or somewhat in insecure situation.

In an example embodiment, a fourth functionality 440 is an extra functionality called EXTRA in FIG. 4. EXTRA 440 may be an extra suite providing miscellaneous applications. Such applications may be for example calculator 441, alarm clock 442, notepad 443 or camera 444, for example.

By selecting the SECURITY application 430, a user may enable positioning capabilities of the location determining component 260. The positioning capabilities may allow a user to display the user's current geographic location on the display 340, map the user's location on the display 340, chart a desired course of travel on the display, or find a desired location on a map generated on the display. In an example embodiment, the monitoring apparatus 120 defines a route and timetable for the portable tracking apparatus 110. User (e.g. a parent) of the monitoring apparatus 120 may follow the progress of the user (e.g. a child) of the portable tracking apparatus 110 in real-time over the wireless network connection 140, 160, 170. In addition, automatic triggers can be made to alarm the monitoring apparatus 120 in case the user of the portable tracking apparatus 110 either moves away for the defined route or is advancing too slowly. Similar approach may be used for defining a certain area by the monitoring apparatus 120 for the portable tracking apparatus 110. In case the user of the portable tracking apparatus 110 moves outside the defined area, an alarm is triggered to the monitoring apparatus 120.

In an example embodiment of the disclosure, the user of the portable tracking apparatus 110 may use the exercise applications 421-423 in a wide variety of situations. No network coverage is necessary needed, neither any external displays nor other electronic equipment. A great benefit of exercise gaming applications is that during the game, user feedback is non-visual (e.g. sound, speech and vibrator), so the player may not require visual contact to display while playing. This significantly enhances the workload of exercises and allows freer movement. Pre-playing user feedback is visual and non-visual, as well as post-playing user feedback. Exercise applications may be downloaded to the portable tracking apparatus 110 in advance either locally using monitoring apparatus connected to the portable tracking apparatus 110 or over the wireless network 160, 170. The user of the portable tracking apparatus 110 may navigate in the menu of the portable tracking apparatus 110 and select a desired exercise application 421-423 under the EXERCISE functionality 420 using touch display 340 or navigation buttons 330.

In an example embodiment, one of such exercise applications 421-423 is a tennis application 421. The portable tracking apparatus 110 may be attached to the wrist or fist of the user for simulating the swinging movements of a tennis racket. When the game starts, the user may be given instructions using both visual and non-visual feedback. During the game, the user is given information on the virtual movement and location of the tennis ball using audible tones from the loudspeaker 240. The audible tones may inform the user of the length, direction and speed of the incoming ball. In addition, the vibrator may be used to inform the user. The power of the vibration may reflect the distance of the incoming ball from the user, for example. The frequency of the audible tones may reflect the direction or speed of the incoming ball. The audible tones may also be synthesized speech instructions sharing the direction, length and speed of the incoming virtual tennis ball.

Based on the received non-visual information relating to the location of the incoming tennis ball, the user of the portable tracking apparatus 110 may move to appropriate direction for getting to the virtual tennis ball for hitting. When the user moves around, both the location of the virtual tennis ball and the location of the user are changed. In response to this, the tennis game application 421 in the portable tracking apparatus 110 may calculate the difference of the virtual tennis ball location and the user location. This calculated difference may be presented to the user continuously using the non-visual information as discussed earlier. As the non-visual information informs that the user is close enough the virtual tennis ball, a hit with the virtual tennis racket may take place. The movement sensor 270 of the portable tracking apparatus 110 senses the movement created by the user when modeling the swinging hit movement by an arm holding the virtual tennis racket. The movement created by the user's arm determines the reply direction and force of the virtual ball. The tennis game application 421 determines the virtual hit to the ball and calculates a feedback to the user based on the force and direction determined. The feedback is given in non-visual form and may contain, for example, an audible tone or a vibration reflecting the quality of the hit. No visual information for the user during the game may be provided at all and all information may be presented to the user non-visually, using loudspeaker and vibrator, for example.

In an example embodiment, a simpler mode of the tennis game may exist. In such mode, only the timing of the hit matters. The non-visual information is presented to the user by the application, informing the virtual distance of the tennis ball from the user. This may take place as discussed earlier. The user should try to hit the virtual tennis ball in correct moment in a similar way as above. This simpler mode may not use the location of the user at all. This would make it possible to play indoors without location determination capability, such as satellite-based positioning.

In an example embodiment, one of such exercise applications 421-423 is a lasso application. The user may start the lasso game and the portable tracking apparatus display 340 may show rope swinging. The display 340 may also show a simple animation of lassoing. Simultaneously, a sound of lassoing may be played on the background. The visual and non-visual instructions may tell the user what should be done during the game. In order to play, the user may raise an arm, to which the portable tracking apparatus 110 is attached, and swing the hand around in large steady circular motion. The feedback sound of rope swinging through the air may be played, in which the type of sound may depend on the speed of the movement, the steadiness of the movement and the size of the circular movement. When the user has reached high speed and steady rhythm he/she may throw his/her arm forward. The user may hear the sound of rope flying through the air. The result of the lasso throw may be expressed through visual and sound feedback, depending on how fast the circular movement was, how steady the user's movement was and how large circular movement the user had. The feedback result expresses how fast animal the user were able to lasso with the lasso throw. For poorest result, a picture of a turtle may be shown with honking sound of turtle. For below average result, a picture of a rooster may be shown and sound of rooster crowing may be played. For average result, a picture of a pig may be shown and a sound of a pig may be played. For above average result, a picture of a horse may be shown and a sound of a horse neighing may be played. For excellent result, a picture of a cheetah may be shown and a sound of a cheetah roaring may be played. No visual information for the user during the game may be provided at all and all information may be presented to the user non-visually, using loudspeaker and vibrator, for example.

In an example embodiment, similar exercise applications may exist, where the virtual object position information is created by the application and presented non-visually to the user. Based on the location and/or the movements of the user, the virtual object position information is updated and presented to the user. The movement of the user is determined and some feedback of the quality of the user's movement relating to the virtual object information is presented, for example non-visually.

In an example embodiment, several applications may be used with some virtual object information, user position and/or movement calculation and feedback determination and presentation to the user, as presented below:

Application: Balance

Virtual object: Hands on your side, lift them up halfway up, forming a cross and keep them there, lift one leg up, on non-visual information change legs lifting the other leg up.

Feedback: Time, accuracy (amount of movement of hands).

Application: Weight lifting (move a stone).

Virtual object: Squat down and put your hands on the ground, stand up and lift your arms up all the way.

Feedback: Kilograms lifted depending on the speed of the movement.

Application: Tennis

Virtual object: Swing your hand from behind of your body forward, backhand and forehand in turns.

Feedback: Points collected like in tennis game, "peep" when its time to hit "cheer" when you win a point, "sigh" when you lose a point.

Application: Golf

Virtual object: Stand sideways and put your hands palm against palm in front of your body, keeping them together lift them up and swing them through.

Feedback: Distance of the hit, hole in one and cheer if you hit a good one.

Application: Football passing (throw ball or javelin)

Virtual object: Stretch your hand backward imaging you have a football in your hand, and throw it forward as if you are making a football pass.

Feedback: Distance of the pass/throw.

Application: Ski jumping

Virtual object: Go into squat position keeping your hands on the side of your body, when your hear "peep" or some other non-visual information, jump as high as you can.

Feedback: Length of jump depending on speed of movement.

Application: High jumping

Virtual object: Run forward and when you hear "peep" or other non-visual information, jump as high as you can.

Feedback: Height jumped depending on the speed of run and jump.

Application: Hopping

Virtual object: Twist your knees a bit and jump in the air, repeat several times Feedback: Amount of jumps, highest jump, and longest jump.

Application: Sledgehammer

Virtual object: Lift your arms on elbow level in front of your body, keep palm against palm, starting spinning around and finally lift your arms as high as you can.

Feedback: distance of sledgehammer throw depending on speed of spinning, time spent spinning and speed of moving your arms.

Application: Frog

Virtual object: Go into squat position putting your hands on the ground in front of your body, when your hear "peep" jump as high as you can.

Feedback: Length of jump depending on speed of movement.

Application: Bowling

Virtual object: Standing up move your whole hand backwards, then swing it fast forward.

Feedback: Strike or normal throw depending on speed and straightness of movement.

Application: Snake

Virtual object: Lift you hands up all the way, move your whole body from ankles to knees, to waist, to elbows and to hands in a snake like motion.

Feedback: Time spent snaking.

Application: Shot put

Virtual object: Squat down with one leg only putting your hand on your cheek, then press towards the opposite direction throwing your hand forward at the same time.

Feedback: Length of shot put depending on the speed of forward movement.

Application: Climb a birch (squirrel)

Virtual object: Make climbing moves by moving your arms rhythmically up and down in turns, stumping with your feet at the same time Feedback: Height and distance climbed depending on amount of climbing movements.

Application: Long jump

Virtual object: Run forward as fast as you can, when you hear "peep", jump as long as you can.

Feedback: Length of jump depending on the speed of run and jump.

Application: Run

Virtual object: Plain simple run, free run or timer attached, different intervals also.

Feedback: Distance, time, KW.

Application: Paddle with birch bark canoe

Virtual object: Put one knee down while keeping the other leg in 90-degree ankle, paddle using both hands and both sides of your body.

Feedback: Distance paddled depending on time used and speed.

Application: Jump from stone to stone

Virtual object: Arrow pointing in the device display which direction you need to jump, length of arrow how long you need to jump.

Feedback: If you jump to stone "cheer" sound and you can continue, if you miss "splash" sound as you fall into water, plus animations.

Figure 5:
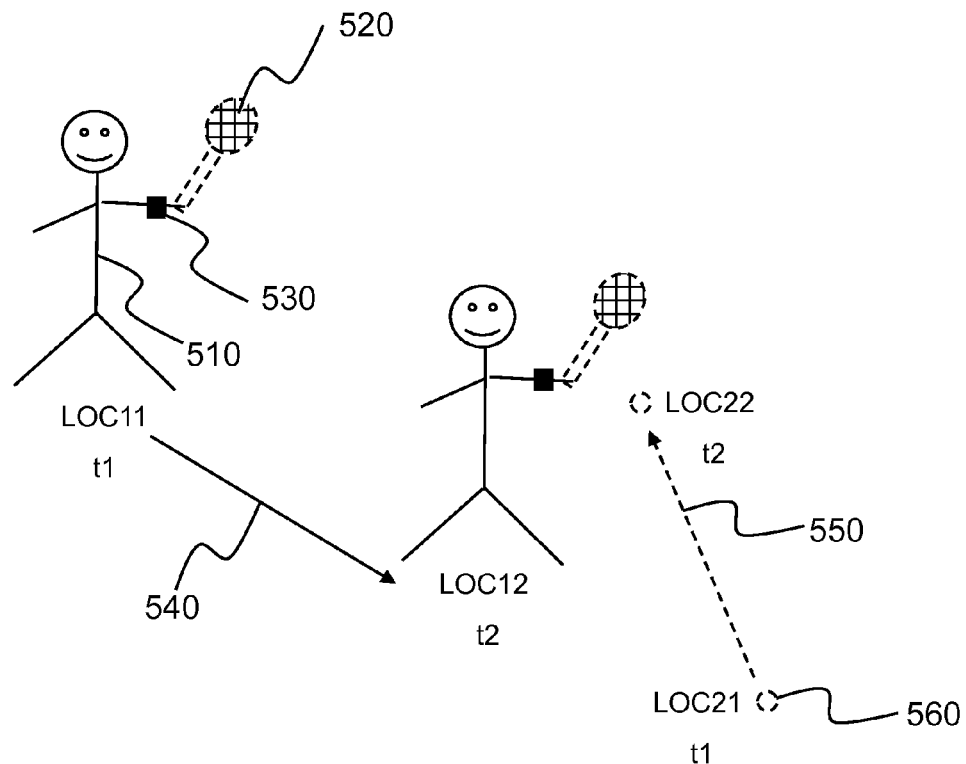
FIG. 5 shows an example embodiment for an exercise application.

FIG. 5 shows an example embodiment for an exercise application. A user 510 is wearing a portable tracking apparatus 110, 530 in accordance with an example embodiment. The portable tracking apparatus 110, 530 may be attached to the wrist or the fist of the user 510 using a strap or a band, for example. First, at time t1, the user 510 is at a location LOC11. The portable tracking apparatus 110, 530 presents to the user 510 non-visual object information relating to the incoming virtual ball 560 from a first virtual location LOC21 at time t1. Based on non-visual object information, the user 510 may move to a direction 540 towards the virtual ball 560. Simultaneously the user 510 receives updated non-visual object information relating to the incoming ball 560, which virtually moves in a direction 550. At time t2, the user 510 is at a location LOC12 and the virtual ball at a virtual location LOC22. The tennis application 421 of the portable tracking apparatus 110, 530 may determine that an appropriate hitting distance for the virtual ball 560 is achieved. Virtual non-visual object information is presented to the user 510 informing that the appropriate hitting distance is achieved. The user 510 may swing the arm, where the portable tracking apparatus 110, 530 is attached, to simulate the hit of the virtual tennis ball 560 with the virtual tennis racket 520. The appropriate hitting window may be available for a certain time period t_hit. T_hit simulates the period of time the user 510 may be able to hit the tennis ball in real tennis. Length of t_hit depends on the speed of the virtual tennis ball 560, the speed of the user 510 and the relative position of the user 510 and the virtual tennis ball 560 from each other, for example.

Figure 6:
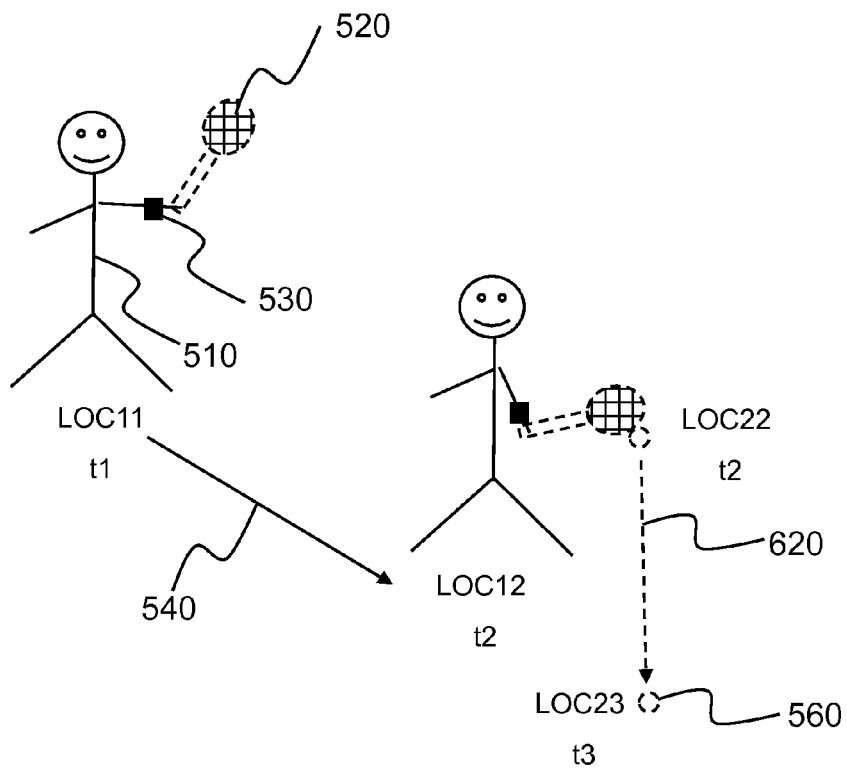

FIG. 6 shows another example embodiment for an exercise application. A user 510 is wearing a portable tracking apparatus 110, 530 in accordance with an example embodiment. The portable tracking apparatus 110, 530 may be attached to the wrist or the fist of the user 510 using a strap or a band, for example. A motion sensor 270 detects the movement of the user's arm modeling the swinging hit. The tennis application 421 may calculate the virtual hit power and direction 620 based on the detected swing movement between times t2 and t3. At time t3, the virtual tennis ball 560 is at a location LOC23 reflecting the quality of the virtual swing. A feedback reflecting the quality of the swing is present non-visually to the user 510.

Playing the same virtual ball 560 may continue until either the user 510 misses the virtual ball 560 or the swing of the user 510 is good enough with power, timing and direction that user 510 wins the ball. After each ball, a score may be output from a loudspeaker of the portable tracking apparatus 110, 530. Different difficulty levels may be defined for the tennis application 421.

The user 510 may also play a training mode of the tennis application 421. In such mode, the user 510 may train the hitting of the virtual tennis ball 560 without movement 540. The portable tracking apparatus 110, 530 presents to the user 510 non-visual object information relating to the incoming virtual ball 560 from the first virtual location LOC21 at time t1. The tennis application 421 of the portable tracking apparatus 110, 530 may determine that an appropriate hitting distance for the virtual ball 560 is achieved. Virtual non-visual object information is presented to the user 510 informing that the appropriate hitting distance is achieved. The user 510 may swing the arm, where the portable tracking apparatus 110, 530 is attached, to model the hit of the virtual tennis ball 560 with the virtual tennis racket 520.

In an example embodiment, the portable tracking apparatus 530 may determine a location of the user 510. The location may be transferred to the operating server 130. In case there are two portable tracking apparatuses 110 in vicinity of each other, one-on-one game may be applicable. The two portable tracking apparatuses 110 may be notified by the operating server 130 of this possibility. After notified, the two portable tracking apparatuses may connect to each other via a wireless connection, for example Bluetooth™. Both portable tracking apparatuses 110 run the same application 421-423 and synchronization for the application 421-423 is carried out over the wireless link. Between the portable tracking apparatuses 110 information on the other apparatus 110 location and movement is transferred.

In an example embodiment, at least two apparatuses 110 may play together over a wireless link. Wireless link may be for example a Bluetooth™ link between the apparatuses. Football game may be one example embodiment. A first user may throw a football pass, wherein the length of the pass may be determined based on the force and the angle of the throw. A second user may receive the length information of the pass to the second apparatus and may start running. During the run, the second user may receive feedback of the run distance via peeping sound, which may get denser as the second user is getting closer to the target length. At target length, the second user may hear a constant peep and may have to jump into the air to make a catch of the football pass.

Another example embodiment may be fencing or light sabre fight: Two users may fence with swords or laser sabres (constant background sound of laser sabres humming). Different movements may be possible: stab (user moves arm forward), smash (user moves arm from up to down), swipe (user moves from left to right or from right to left). The force of the movement may depend on the speed. Both users may move their arm at the same time. If they make same movement (stab, swipe or smash), feedback sound of laser sabres crashing together may be provided with vibration effects. If the movements are different, then another user win a point and feedback sound of scoring may be played. Following criteria may be used: Stab wins smash, smash wins swipe and swipe wins stab. The fight may continue until one of the users wins 10 times.

Figure 7:
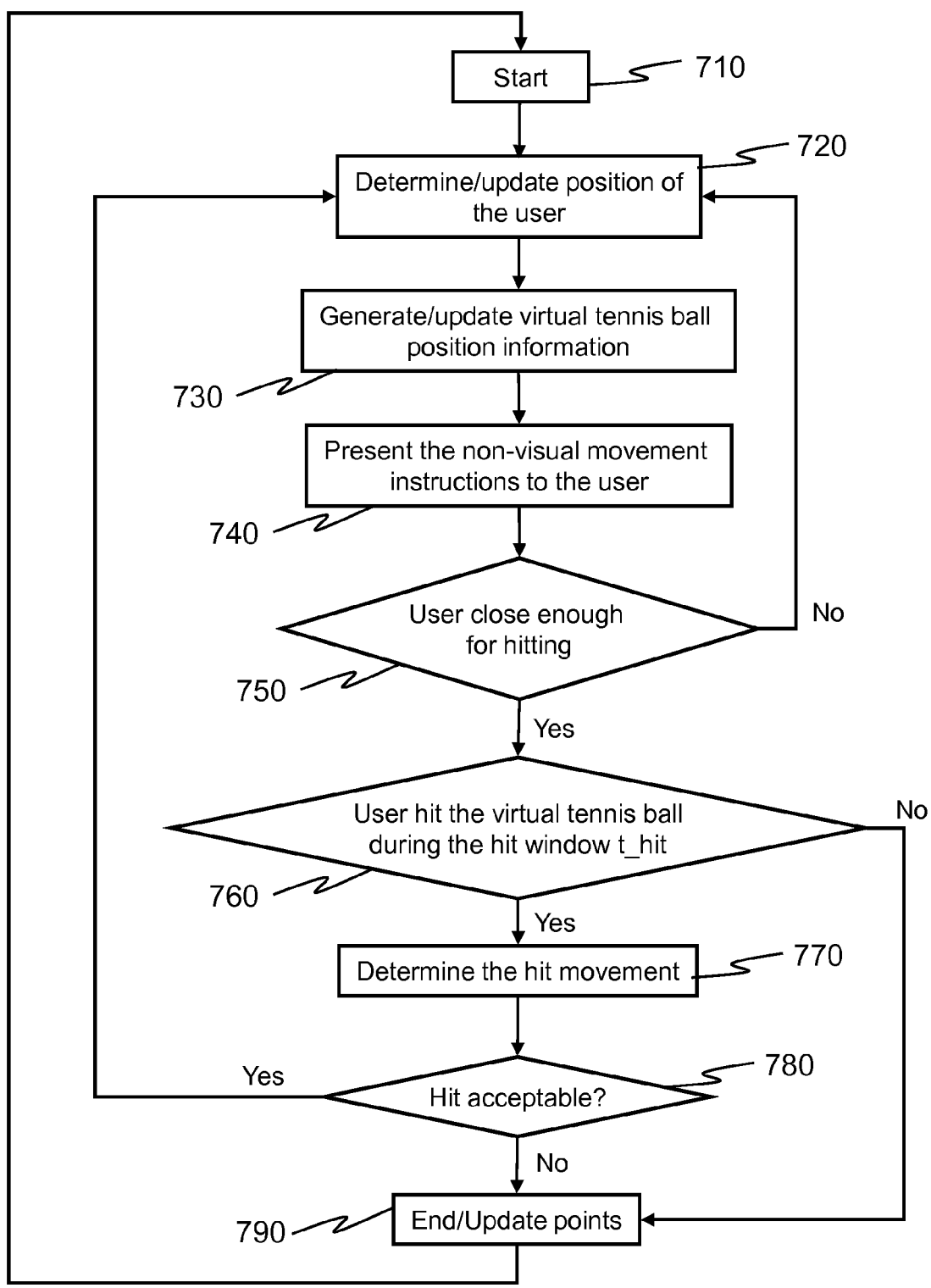
FIG. 7 shows a flow diagram of an example embodiment for an exercise application of tennis.

FIG. 7 shows a flow diagram of an example embodiment for an exercise application of tennis 421. The user 510 may start 710 the tennis application 421 from the menu structure of the portable tracking apparatus 110, 530 utilizing the user interface 330, 340 of the portable tracking apparatus 110, 530. The tennis application 421 determines the position 720 of the user by determining the position of the portable tracking apparatus 110, 530 using the location determining component 260 of the portable tracking apparatus 110, 530. Virtual tennis ball position information is generated 730 by the tennis application 421 based on the virtual modeling of the virtual tennis ball 560. In step 740, the non-visual movement instructions are presented to the user 510. Such instructions may comprise audio tones or vibration presenting the distance of the virtual tennis ball 560 from the user 510. Audio tones may be generated in such a way, that the closer the virtual ball 560 is to the user 510, the louder is the audio tone. Another option may be that the closer the ball gets, the denser the sound gets, and at target, the sound may be constant. Still another option may be that the closeness may be presented in form of vibration—the closer the ball is, the stronger the vibration. The balance of the audio between the left and right audio channel from the audio output of the portable tracking apparatus 110, 530 may correspond to the direction of the incoming virtual ball 560. Another example embodiment may comprise non-visual movement instructions that comprise audio instructions of the direction and distance of the virtual tennis ball 560. Such audio instructions may comprise for example synthesized speech samples like "left", "right", "1 meter", "2 meters", "3 meters" and so on. In step 750, the tennis application 421 determines if the user 510 is close enough for hitting the virtual tennis ball 560. When the user 510 is close enough to the virtual tennis ball 560 for hitting, a timer t_hit is triggered. During the time t_hit the user 510 is able to hit the virtual tennis ball 560. If the user 510 is not close enough for hitting, the position of the user 510 is updated 720 and the position of the virtual tennis ball 560 is updated before re-evaluating the proximity 750 of the virtual tennis ball 560.

In case the user 510 is close enough for hitting, the tennis application 421 determines the hitting 760 with the help of the portable tracking apparatus 110, 530 movement sensor 270, for example. If the user 510 misses the hit, the tennis application proceeds to the end step 790 for next point and updates the possible score before starting 710 next point. When the user 510 hits the virtual tennis ball 560 during the time window t_hit, the hit movement 770 is determined by the tennis application 421. Determination may be based on at least one of the following criteria: user speed, virtual ball speed, force used when hitting the virtual ball, timing of the hitting and angle of the hit. User speed may be generated based on location determining component 260, virtual ball speed may be generated based on the tennis application 421 and the force used as well as the angle when hitting the virtual ball based on the movement sensor 270 of the portable tracking apparatus 110, 530. Timing of the hitting may be determined by the tennis application 421 based on the time window t_hit and the movement sensor 270. Optimal hitting time may be determined to be in the middle of the time window t_hit. Hitting the virtual ball 560 in the middle of the time window t_hit produces more power and/or accuracy to the shot. Hitting the virtual ball with an angle that starts a bit below the waistline and ends a bit above the waistline following through the motion may produce the best shots. Similar kind of approach may be used for other exercise games 421, 422, 423.

Figure 8:
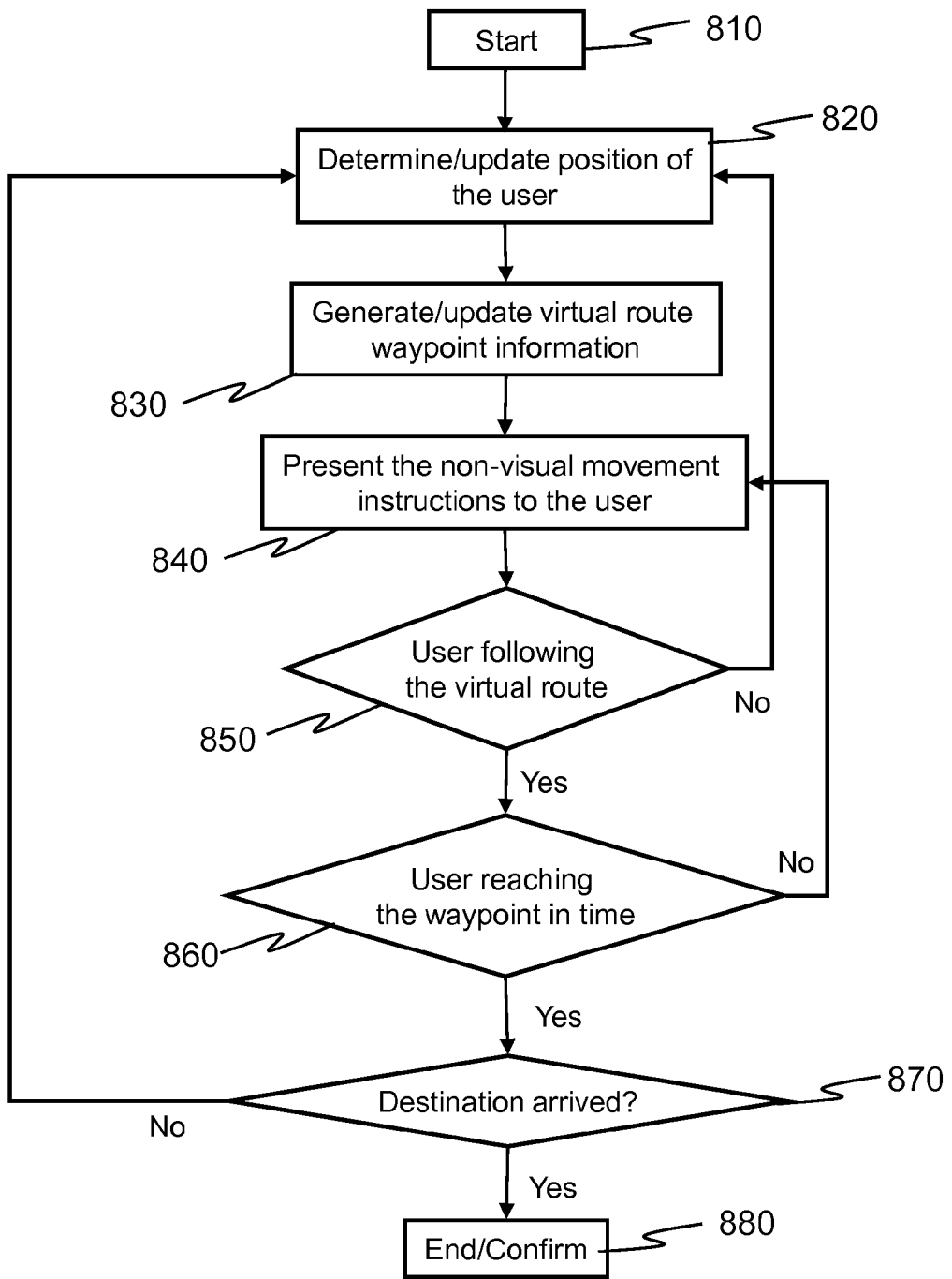
FIG. 8 shows a flow diagram of an example embodiment for an security application.

FIG. 8 shows a flow diagram of an example embodiment for a security application of safe route 431. The user 510 may start 810 the safe route application 431 from the menu structure of the portable tracking apparatus 110, 530 utilizing the user interface 330, 340 of the portable tracking apparatus 110, 530. Safe route application 431 may also be triggered by a remote client 120. Remote client 120 may set and monitor a specific route for the user 510 of the portable tracking apparatus 110, 530 to follow. The safe route application 431 determines 820 the position of the user by determining the position of the portable tracking apparatus 110, 530 using the location determining component 260 of the portable tracking apparatus 110, 530. Virtual route waypoint information is generated 830 by the safe route application 431 based on the waypoints defined for the virtual route. In step 840, the non-visual movement instructions are presented to the user 510. Such instructions may comprise audio tones presenting the distance to the next virtual waypoint 560 from the user 510.

Audio tones may be generated in such a way, that the more distant the virtual route waypoint is to the user 510, the louder is the audio tone. A further criterion for the volume of the audio tone may be the time schedule calculated by the safe route application 431. Each waypoint of the virtual route may have a defined timing criterion the user should meet. The criterion is based on the distance of the waypoint versus to the average speed of the user of the portable tracking apparatus 110. In case the user of the portable tracking apparatus 110 is not traveling in certain route at certain speed as specified by the client 120, an alarm may be triggered. By doing this, the client 120 is being informed in case the portable tracking apparatus user 510 is moving too slow. This might mean that the user 510 of the portable tracking apparatus is in danger or somewhat in insecure situation. The non-visual movement instructions 840 may comprise the distance to the next waypoint, for example a junction or a landmark, or direction to take in the junction. An example embodiment may comprise non-visual movement instructions 840 that comprise audio instructions of the direction and distance of the virtual route waypoint. Such audio instructions may comprise for example synthesized speech samples like "left", "right", "100 meters", "200 meters", "300 meters" and so on. In step 850, the safe route application 431 determines if the user 510 is following the defined virtual route. The virtual route may comprise a limit how much the user 510 may deviate from the virtual route. In case the user 510 deviates from the route more than preferred by the remote client 120, alert actions may take place. First, the user 510 may be notified with higher volume of the deviation. Second, the remote client 120 may be notified of the deviation. Third, the position of the user 510 is further updated and the user 510 is notified of the deviation until the user 510 returns to the defined virtual route.

The user 510 may be defined a time schedule for each waypoint. Such schedule may be defined by the remote client 120 or the safe route application 431 of the portable tracking apparatus 110. In step 860, the time schedule of reaching waypoints is followed. In case the user 510 is late for reaching the waypoint in time or is running behind the time schedule in average speed, the user 510 may be re-presented the non-visual movement instructions 840. If the user 510 reaches the waypoint in time, the safe route application 431 checks the arrival to the destination 870. If the defined virtual route still comprises additional waypoints, actions like updating user position 820 and determining next waypoint and time schedule for reaching the waypoint 830 are carried out. If the destination is reached, the routing is ended 870 and confirmation may be sent to the remote client, for example.

The remote client 120 may monitor the progress of the user 510 wearing the portable tracking apparatus 110 in real-time. The virtual route and the progress of the user 510 may be presented. The remote client 120 may define alerts in any waypoint of the virtual route. Such alert may comprise status update of the portable tracking apparatus 110 location information and average speed information. The remote client 120 may also set targets and/or alerts for the user of the portable tracking apparatus 110 in relation to exercise games. The user of the remote client 120 may set a target time or game application for playing an exercise game, for example. The remote client 120 may also set up monitoring functionality to an operating server 130. Such functionality may comprise specific parameters for the portable tracking apparatus 110 in relation to security or exercise. Thus, no matter the remote client 120 is not active, the operating server functionality may follow the progress of the portable tracking apparatus 110. Such following may include setting targets and/or alerts for the user of the portable tracking apparatus 110 and following the user progress in view of the targets, including presenting feedback to the user of the portable tracking apparatus 110.

Figure 9:
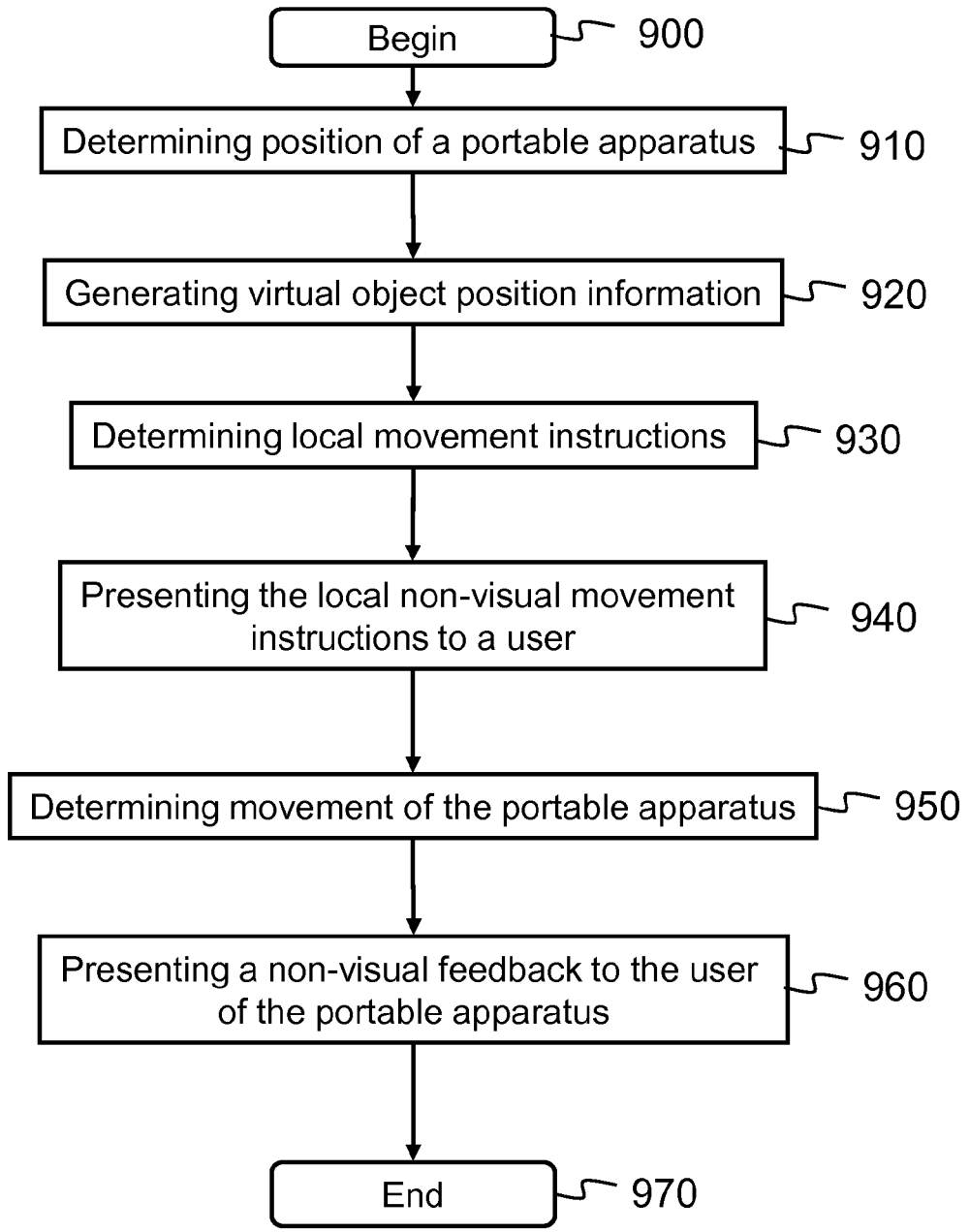
FIG. 9 shows a flow diagram of operations in an apparatus in accordance with aspects of the disclosed embodiments.

FIG. 9 shows a flow diagram of operations in an apparatus in accordance with an example embodiment. In step 900, the method is started. In step 910, position of a portable tracking apparatus is determined. Next, virtual object position information is generated in step 920. In step 930, local non-visual movement instructions are determined based on the determined position and the generated virtual object position information. In step 940, the local non-visual movement instructions to a user of the portable tracking apparatus is presented. In step 950, movement of the portable tracking apparatus is determined. In step 960, a non-visual feedback to the user of the portable tracking apparatus is presented based on the movement of the portable tracking apparatus. The method ends in step 970.

Various embodiments have been presented. It should be appreciated that in this document, words comprise, include and contain are each used as open-ended expressions with no intended exclusivity.

The foregoing description has provided by way of non-limiting examples of particular implementations and embodiments a full and informative description of the best mode presently contemplated by the inventors for carrying out the invention. It is however clear to a person skilled in the art that the invention is not restricted to details of the embodiments presented above, but that it can be implemented in other embodiments using equivalent means or in different combinations of embodiments without deviating from the characteristics of the invention.

Furthermore, some of the features of the above-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

What is claimed is:

1. A method for tracking movements in a portable tracking apparatus including a movement sensor, the method comprising:
   generating virtual object position information;
   determining local movement instructions for a user of the portable tracking apparatus based on the generated virtual object position information;
   presenting only non-visually the local movement instructions to the user;
   determining movement of the portable tracking apparatus using the movement sensor;
   presenting a non-visual feedback to the user of the portable tracking apparatus determining a position of the portable tracking apparatus using at least one of the following: global positioning system, cellular positioning system, non-cellular positioning system and motion sensor;
   determining a starting position of the user in a game application based on the determined position of the portable tracking apparatus;
   determining a virtual game object position based on the generated virtual object position information; and
   generating audio tones for the user based on the determined local non-visual movement instructions and feedback based on the determined movement of the portable tracking apparatus.

2. The method of claim 1, wherein the virtual object position information being at least one of the following:
   a virtual object of a game application;
   a virtual route for the user to follow; and
   a virtual waypoint of the virtual route.

3. The method of claim 1, wherein the virtual object position information being generated by a remote apparatus connected remotely to the portable tracking apparatus.

4. The method of claim 1, wherein
   the determined movement of the portable tracking apparatus comprises at least one of the following:
   determining an angle of the movement;
   determining a speed of the movement;
   determining a length of the movement;
   determining time lapsed for the movement;
   determining timing of the movement;
   determining trajectory of the movement; and
   determining a position after the movement.

5. The method of claim 1, wherein the non-visual feedback to the user is further based on at least one of the following:
   deviation of the user from the virtual route or from the virtual waypoint;
   time lapsed;
   direction of the user on the virtual route;
   a relation of the determined movement to the virtual object position information of a game application.

6. The method of claim 5, wherein the relation of the determined movement to the virtual object position information of a game application is based on at least one of the following:
   timing of the determined movement; and
   direction of the movement.

7. The method of claim 1 further comprising presenting the local movement instructions and feedback using audio tones.

8. The method of claim 1 further comprising presenting the local movement instructions and feedback using tactile feedback.

9. The method of claim 1, wherein the movement sensor is an accelometer.

10. The method of claim 1, wherein the movement sensor is a gyro.

11. The method of claim 1, further comprising:
determining a starting position of the user for a virtual route comprising at least one waypoint in a security application based on the determined position of the portable tracking apparatus;
determining virtual route waypoint position based on the generated virtual object position information;
generating audio tones for the user based on the determined local non-visual movement instructions and feedback;
determining a deviation of the user position compared to the virtual route and updating the determined local non-visual feedback if the deviation exceeds a threshold set by the security application; and
determining a target time for the user to reach the determined waypoint and calculating time spent for the user; and
updating the determined local non-visual feedback if the time spent exceeds the target time.

12. A portable tracking apparatus comprising:
a loudspeaker configured to present non-visual movement instructions and feedback to a user of the portable tracking apparatus;
a movement sensor operative to detect a movement of the portable tracking apparatus at least one of global positioning system, cellular positioning system, non-cellular positioning system operative to detect a position of the portable tracking apparatus;
at least one processor;
at least one memory including computer program code, the at least one memory and the computer program code configured to, with the at least one processor, cause the apparatus at least to perform:
generate virtual object position information;
determine local movement instructions for the user based on the generated virtual object position information;
present only non-visually the local movement instructions to the user;
determine movement of the portable tracking apparatus using the movement sensor;
present a non-visual feedback to the user of the portable tracking apparatus based on the determined movement of the portable tracking apparatus determining a starting position of the user in a game application based on the determined position of the portable tracking apparatus;
determining a virtual game object position based on the generated virtual object position information; and
generating audio tones for the user based on the determined local non-visual movement instructions and feedback.

13. The apparatus of claim 12 wherein the movement sensor is at least one of an accelometer or a gyroscope.

14. The apparatus of claim 12 further comprising a vibrator operative to provide the non-visual feedback to the user using tactile feedback.

15. The apparatus of claim 12 further comprising a tamper detector configured to detect an attempt to remove the portable tracking apparatus from the user body.

16. The apparatus of claim 15, wherein the tamper detector comprises at least one of the following: a thermal sensor for sensing body temperature of the user and a wire through a strap of the portable tracking apparatus.

17. A computer program embodied on a non-transitory computer readable medium comprising computer executable program code which, when executed by at least one processor of a portable tracking apparatus, causes the portable tracking apparatus to perform:
generate virtual object position information;
determine local movement instructions for the user based on the generated virtual object position information;
present only non-visually the local movement instructions to the user;
determine movement of the portable tracking apparatus using the movement sensor;
present a non-visual feedback to the user of the portable tracking apparatus based on the determined movement of the portable tracking apparatus determining a position of the portable tracking apparatus using at least one of the following: global positioning system, cellular positioning system, non-cellular positioning system and motion sensor;
determining a starting position of the user in a game application based on the determined position of the portable tracking apparatus;
determining a virtual game object position based on the generated virtual object position information; and
generating audio tones for the user based on the determined local non-visual movement instructions and feedback.

* * * * *